(12) United States Patent
Pahlberg et al.

(10) Patent No.: US 7,875,015 B2
(45) Date of Patent: *Jan. 25, 2011

(54) MEDICAL CONTAINER WITH IMPROVED PEELABLE SEAL

(75) Inventors: Olof Pahlberg, Bällinge (SE); Johan Engholm, Solna (SE); Manus O'Donnell, Hägersten (SE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 42 days.

This patent is subject to a terminal disclaimer.

(21) Appl. No.: 11/658,896

(22) PCT Filed: Jun. 16, 2005

(86) PCT No.: PCT/EP2005/006475

§ 371 (c)(1),
(2), (4) Date: Jun. 11, 2007

(87) PCT Pub. No.: WO2006/010411

PCT Pub. Date: Feb. 2, 2006

(65) Prior Publication Data

US 2008/0017543 A1 Jan. 24, 2008

(30) Foreign Application Priority Data

Jul. 29, 2004 (EP) .................. 04017921

(51) Int. Cl.
*B65D 25/08* (2006.01)
*A61B 19/00* (2006.01)
*A61M 5/32* (2006.01)

(52) U.S. Cl. ................ 604/410; 604/416; 206/219

(58) Field of Classification Search ............... 206/219, 206/221, 222, 484, 484.2; 604/409, 410, 604/416
See application file for complete search history.

(56) References Cited

U.S. PATENT DOCUMENTS

| 3,257,072 A | 6/1966 | Reynolds |
| 3,964,604 A * | 6/1976 | Prenntzell .................. 206/219 |
| 4,331,264 A | 5/1982 | Staar |

(Continued)

FOREIGN PATENT DOCUMENTS

CA 2393039 6/2001

(Continued)

OTHER PUBLICATIONS

International Search Report for PCT/EP2005/006475, dated Aug. 2005, 4 pages.

(Continued)

*Primary Examiner*—Mickey Yu
*Assistant Examiner*—Melissa L Lalli
(74) *Attorney, Agent, or Firm*—Kenyon & Kenyon LLP

(57) ABSTRACT

A pharmaceutical container with an improved peelable seal is provided, wherein the container may be made of a flexible polymeric film and comprises at least one peelable seal comprising at least two substantially straight sections which are connected by a rupture zone (5), The rupture zone of the peelable seal may be curved over its whole length between the straight sections. The container may be used for storing pharmaceutical substances, solutions for dialysis, solutions for infusion and/or agents for nutrition.

11 Claims, 7 Drawing Sheets

U.S. PATENT DOCUMENTS

| | | | |
|---|---|---|---|
| 4,396,383 A * | 8/1983 | Hart | 604/518 |
| 4,465,488 A | 8/1984 | Richmond et al. | |
| 4,484,920 A | 11/1984 | Kaufman et al. | |
| 4,602,910 A * | 7/1986 | Larkin | 604/87 |
| 4,759,472 A * | 7/1988 | Strenger | 222/92 |
| 4,952,068 A | 8/1990 | Flint | |
| 4,997,083 A | 3/1991 | Loretti | |
| 5,061,236 A | 10/1991 | Sutherland | |
| 5,195,658 A | 3/1993 | Hoshino | |
| 5,209,347 A | 5/1993 | Fasbisiewicz et al. | |
| 5,263,609 A * | 11/1993 | Hoshino | 222/92 |
| 5,431,496 A | 7/1995 | Balteau et al. | |
| 5,560,403 A * | 10/1996 | Balteau et al. | 141/9 |
| 5,783,269 A | 7/1998 | Heilmann et al. | |
| 5,928,213 A | 7/1999 | Barney et al. | |
| 6,007,529 A | 12/1999 | Gustafsson et al. | |
| 6,017,598 A | 1/2000 | Kreischer et al. | |
| 6,039,719 A | 3/2000 | Wieslander et al. | |
| 6,039,720 A | 3/2000 | Wieslander | |
| 6,074,366 A | 6/2000 | Rogers et al. | |
| 6,095,355 A | 8/2000 | Jessen et al. | |
| 6,146,360 A | 11/2000 | Rogers et al. | |
| 6,186,998 B1 * | 2/2001 | Inuzuka et al. | 604/410 |
| 6,231,559 B1 | 5/2001 | Loretti | |
| 6,319,243 B1 | 11/2001 | Becker et al. | |
| 6,398,771 B1 * | 6/2002 | Gustafsson et al. | 604/410 |
| 6,416,496 B1 | 7/2002 | Rogers et al. | |
| 6,468,259 B1 | 10/2002 | Loretti et al. | |
| 7,055,683 B2 | 6/2006 | Bourque et al. | |
| 7,169,138 B2 | 1/2007 | Becker et al. | |
| 7,175,614 B2 | 2/2007 | Gollier et al. | |
| 7,306,095 B1 | 12/2007 | Bourque et al. | |
| 7,458,741 B2 * | 12/2008 | Detwiler et al. | 401/132 |
| 2001/0000042 A1 | 3/2001 | Inuzuka et al. | |
| 2003/0036743 A1 | 2/2003 | Becker et al. | |
| 2003/0040708 A1 | 2/2003 | Rogers et al. | |
| 2004/0118710 A1 | 6/2004 | Bourque et al. | |
| 2004/0134802 A1 | 7/2004 | Inoue et al. | |
| 2007/0029001 A1 | 2/2007 | Trouilly et al. | |
| 2007/0031976 A1 | 2/2007 | Trouilly et al. | |
| 2007/0092579 A1 | 4/2007 | Trouilly et al. | |
| 2008/0004594 A1 | 1/2008 | Pahlberg et al. | |

FOREIGN PATENT DOCUMENTS

| | | |
|---|---|---|
| EP | 0228819 | 7/1987 |
| EP | 0700280 | 3/1996 |
| EP | 0739713 | 10/1996 |
| EP | 0811560 | 12/1997 |
| JP | 5-16635 | 3/1993 |
| JP | 8-182739 | 7/1996 |
| JP | 2000-504956 | 4/2000 |
| JP | 2001-522655 | 11/2001 |
| WO | WO 97/37628 A | 10/1997 |
| WO | WO9737628 | 10/1997 |
| WO | 9816183 | 4/1998 |
| WO | 9924086 | 5/1999 |
| WO | WO0142009 | 6/2001 |
| WO | WO 2004/047714 A1 | 6/2004 |
| WO | 2006/010410 A1 | 2/2006 |

OTHER PUBLICATIONS

International Search Report for PCT/EP2005/006474 dated Nov. 14, 2005.
U.S. Appl. No. 11/658,899, filed Jun. 11, 2007, pending.
Non-Final Office Action in U.S. Appl. No. 11/658,899, issued Sep. 30, 2008.
Examiner Interview Summary in U.S. Appl. No. 11/658,899, issued Feb. 5, 2009.
Final Office Action in U.S. Appl. No. 11/658,899, issued May 14, 2009.
Non-Final Office Action in U.S. Appl. No. 11/658,899, issued Sep. 18, 2009.
International Search Report PCT/EP2005/006475, issued Sep. 1, 2005.
Written Opinion, PCT/EP2005/006475, issued Jan. 30, 2007.
Written Opinion, PCT/EP2005/006474, issued Jan. 30, 2007.
Office Action mailed Mar. 5, 2010 in U.S. Appl. No. 11/658,899.
Notice of Allowance in U.S. Appl. No. 11/658,899, issued Jul. 7, 2010.
Advisory Action in U.S. Appl. No. 11/658,899, issued Jul. 24, 2009.
Allowed Claims in U.S. Appl. No. 11/658,899.
Japanese Office Action, Application No. JP 2007-522932, mailed on Aug. 31, 2010.

* cited by examiner

Prior Art Fig. 4
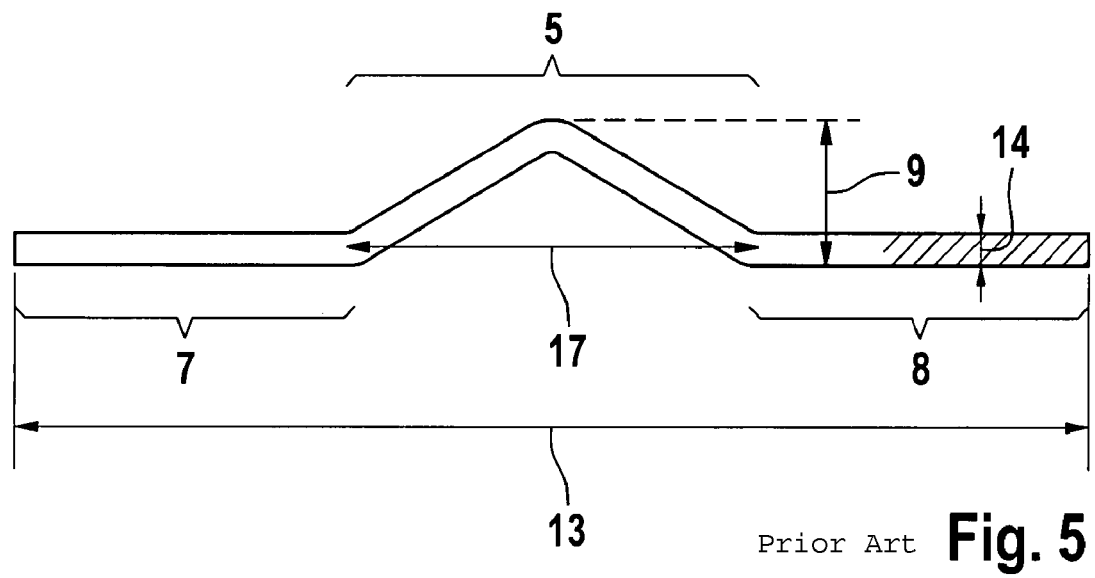
Prior Art Fig. 5
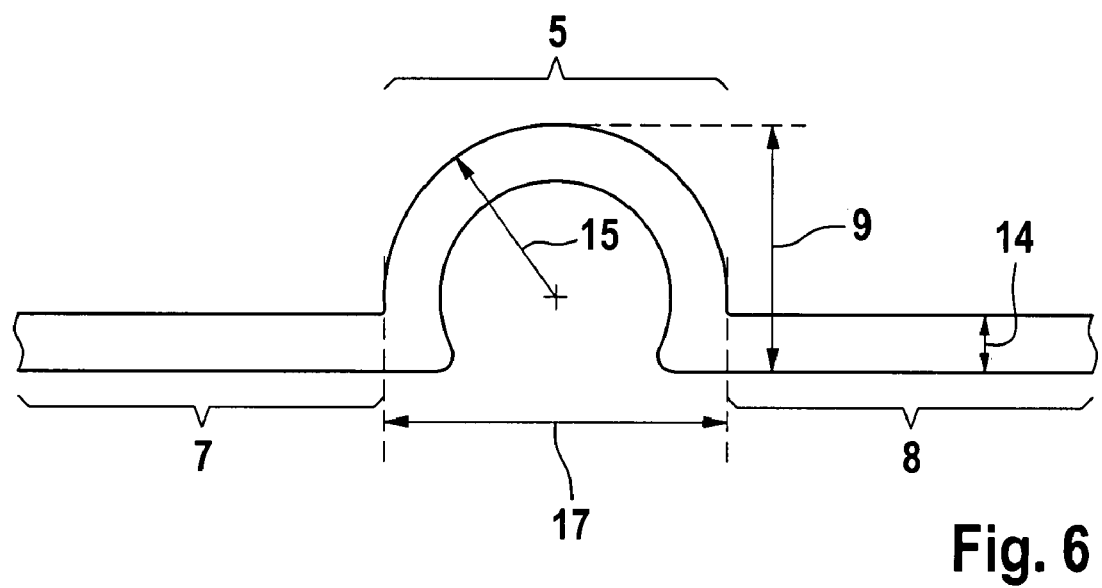
Fig. 6

MEDICAL CONTAINER WITH IMPROVED PEELABLE SEAL

FIELD OF THE INVENTION

The present invention relates to a container for storage of pharmaceutical agents, which has a peelable seal with a curved rupture zone that is easy to open even at high seal strengths. Furthermore, the present invention relates to a method for producing said container and to the use of said container for storing pharmaceutical substances, solutions for dialysis, solutions for infusion and/or agents for nutrition.

BACKGROUND OF INVENTION

Flexible containers from polymer films are widespread for storing pharmaceutical substances solutions for dialysis, solutions for infusion and/or agents for nutrition. For opening filled containers or compartments of said containers, several materials and methods for producing peelable seals (peelable heatsealed welds) have been developed. In contrast to permanent welded seals, peelable seals can be ruptured by tensile force or by pressing on an adjacent container chamber that is filled with a liquid. It should be guaranteed to open the seal without damages to the container material or leakage. The peelable seal strength should be high enough for production and transport and still low enough to easily open the bag.

In order to simplify the opening of peelable seals, such seals have been provided with so-called rupture zones, whereby the opening force is locally reduced and the manual opening of the peelable seals is facilitated. Such seal can readily be opened by different handling techniques.

European patent document EP 0 700 280 concerns a multi-layer polymer film for a multi-chamber medical bag for preparation of mixed medical solutions, which has at least two chambers which are separated from each other by a peelable seal. European patent document EP 0 700 280 suggests a V-shaped rupture zone. In this case, the seal opens first at the point of the V since the highest force on the seal is created there.

European patent document EP 0 893 982/International Publication Number WO97037628 relates to flexible polymeric containers with an improved long term storage capacity for parenterally administered medical fluids. The container comprises an outer sealed airtight envelope and an inner container filled with one or several medical agents. The inner container comprises peelable seals having rupture zones. The rupture zones of the peelable seals are V-shaped and, therefore, comprise a point where two straight seams meet in an angle. A small or sharp angle will be easy to rupture by the user, but it will at the same time create a risk for unintentional opening when handling the container. In contrast, a very large angle will provide a seam that is difficult to open. Therefore, European patent document EP 0 893 982 suggests an angle of the seals in the rupture zone of 120° to 140°.

A first preferred opening procedure mentioned in European patent document EP 0 893 982 is to gently roll up the container from the upper side and thereby make use of the volume of the largest chamber to exert a pressure large enough to rupture the seal in its weakest point and peel apart the seam towards the sides of the container. This technique is designated as the rolling method. Another preferred way of opening the seal is to pull the front and the rear walls of the inner container apart from one another by a careful pulling motion so a rupture is formed in the weakest spot of the seal which thereby may be easy to peel apart. This technique is designated as the pulling method.

The document further describes a rupture zone having two straight seams meeting in a region formed as a curved part. The rupture zone still comprises straight sections.

The two most common complaints concerning medical containers with a peelable seal are: (1) peelable seals are already opened at arrival to customer and (2) a film failure when opening peelable seals.

There is always a balance between the demands to have a peelable seal that is strong enough to withstand the manufacturing process and is easy to open for the customer. Flexible containers with peelable seals of low seal strength, e.g. 5 to 10 N/30 mm, can be readily opened, but seals of low strength can be damaged during manufacturing and transport.

For this reason, it is advantageous to manufacture peelable seals with a seal strength at least 30 N/30 mm, and preferably 40 N/30 mm. However, the inventors have found that the polymeric film is frequently torn when the peelable seal with a V-shape as disclosed in European patent document EP 0 893 982 and a strength of at least 30 N/30 mm is opened by the pulling method, resulting in leakages in the bag. This problem might be avoided by using the rolling method, which should allow a more controlled opening by applying a more even pressure on the weak seal.

The inventors have, however, found that the V-shaped rupture zone according to EP 0 893 982 shows a relatively high resistance against manual opening of the seals by the rolling method when the seal strength is equal or higher than 30 N/30 mm.

High resistance against opening means that a higher burst pressure registered inside the liquid-filled bag is required for opening the seal. It is a major drawback for the user in daily routine when a relatively high burst pressure is required for opening peelable seals. Thereby, the handling of the bag is impaired. By applying a high burst pressure, the seal opens rapidly in one step instead of opening at first in the rupture zone and peeling slowly apart towards the sides of the container in a second step.

When a container with three chambers is used which are filled with different solutions, a sudden and fast opening of peelable seals is undesirable, because it is not possible to control which seal is opened at first. Even though the bag-design is the most important point for a controlled mixing order of the chambers contents, an uncontrolled opening of the seals as mentioned above might also result in a uncontrolled mixing of the bag contents.

In order to reach a controlled opening of the peelable seals, it is desired that the rupture zone opens in a first step and in a second step the remaining part of the peelable seal opens. Experiments of the inventors have shown that this can hardly be reached with conventional V-shaped seals, especially when V-shaped seals are hard to open due to high seal strengths of at least 40 N/30 mm.

An object of the present invention is to provide a container with a peelable seal that can be readily opened without the danger of destroying the container. In particularly, it is an object of the present invention is to provide a flexible container with a well functioning peelable seal design, wherein the seal should be easy to open when the seal strength is ≦40 N/30 mm; the seal should not open by slight pressure on the bag that occurs during storage and transport; the seal should not open rapidly and in one step, the seal may open in two steps—first the rupture zone and then the remaining part; and the seal should open by rolling as long as the seal is peelable—in this case, the seal should easily open up to seal strengths of 40 N/30 mm.

The above mentioned objects may be attained by a container made of a flexible polymeric film comprising at least one peelable seal having at least two substantially straight sections which are connected by a rupture zone, wherein the rupture zone of the peelable seal is curved over its whole length between the straight sections.

The one or more rupture zones of the peelable seal connect substantially straight sections of the peelable seal. Substantially straight means that said sections can either be absolutely straight or minimally bent with respect to the dimensions of the container. Preferably, the sections that are connected by the curved rupture zone are absolutely straight.

A peelable seal according to the present invention can contain more than one rupture zone and more than two straight sections. However, it is preferred that it contains two straight sections that are connected by one rupture zone. In the latter case, the rupture zone is, in a specific preferred embodiment located in the middle of the peelable seal, resulting in two straight sections of equal length.

The rupture zone of the peelable seal is curved over its whole length between the straight sections. The term curved means that there are neither straight sections nor any kinks or angles within the rupture zone. A curved shape according to the present invention comprises circular shapes, S-shapes and ellipsoidal shapes and irregular curved shapes, wherein circular and ellipsoidal shape mean that the curved rupture zone is formed as an arc of a circle or an arc of an ellipse. It is to be understood in this connection that the terms "arc of an circle" or "arc of an ellipse" are equivalent to a segment of a circle or segment of an ellipse.

In an embodiment of the invention, the curved rupture zone of the seal is formed as an arc of a circle with a radius of 5 to 75 mm, more preferably 10 to 30 mm and most preferably 20 to 25 mm, wherein the radius is measured from the center of the circle to a point on the outer edge of the seal, wherein the outer edge is the edge that is more dislodged from the central point of the circle than the inner edge.

When the curved rupture zone is formed as an arc of a circle, said arc has preferably a central angle of at least 60°, more preferably 60° to 180°, especially 90° to 150°.

It is also advantageous that the rupture zone is S-shaped, wherein a preferred S-shape is made up of two connected half circles with a radius of 5 to 75 mm, more preferably 10 to 30 mm and most preferably 20 to 25 mm. The radius is again measured from the center of the circle to an outer edge of the seal.

The straight sections of the peelable seal can enclose an angle or the sections can be parallel to each other or in line with each other. When the straight sections form an angle, such angle is preferably from 120° to 180° and more preferably from 150° to 180°.

When the straight sections are parallel to each other, the distance (dislocation) between the straight parallel sections is preferably from 10 to 60 mm, more preferably 15 to 40 mm and most preferably 20 to 35 mm.

In an embodiment of the invention, the curved rupture zone is formed as an arc of a circle with a central angle of 90° and the straight sections are parallel to each other.

The width of the seal can vary between the straight sections and the rupture zone. In absolute values the seal width of the straight sections is preferably from 2 to 10 mm, more preferably from 5 to 8 mm, and the seal width of the rupture zone is from 2 to 10 mm, preferably from 5 to 8 mm. The width of the straight sections may be different than the width of the rupture zone. Preferably, however, the seal width of the straight sections and the seal width of the rupture zone are the same.

The rupture zone is preferably positioned in the middle of the seal, so it can be successively opened from the middle towards the sides, since this may enable a highly reproducible opening procedure by the user from the outside of the bag.

The rupture zone typically has a length of less than half the entire seal, preferably less or equal than about 40% of the seal and more preferably less than about 30% of the seal length. In a more preferred embodiment of the present invention, the length of the rupture zone amounts to 3 to 10%, more preferably 5 to 7% of the length of the peelable seal. But it can also be advantageous when length of the rupture zone is 7 to 13%. In absolute values, the length of the rupture zone is preferably 20 to 40 mm.

In an embodiment of the invention, the container is made of a flexible polymeric film having a region with a higher melt point designated as its outside and having a region with lower melt point designated as its sealing inside which can be sealed together by means of conventional welding tools to permanent or peelable seals. It is to be understood that the inner region is intended to face the stored agent or agents and can form both permanent seals and different peelable seals when subjected to different welding conditions or operations.

The film may be made of at least two different polymer layers wherein the inside layer is a sealant layer that is capable of forming both permanent seals and peelable seals when subjected to welding at different temperatures.

A preferred multilayer polymer material for the manufacture of a container according to the present invention is described in European patent document EP 0 739 713 and known under the trademark Biofine™.

Another multilayer polymer material can have the following structure:

The inner sealant layer is preferably based on polyolefins, such as polyethylenes or polypropylenes of various qualities which are chemically inert to the stored fluids, autoclavable, weldable and possible to recycle. The terms "polyethylenes" and "polypropylenes" are intended to include both homopolymers and copolymers having such mentioned characteristics unless otherwise is specified. Preferably, the sealant layer is based on a polyethylene homopolymer, a polyethylene copolymer, a polypropylene homopolymer, a polypropylene copolymer a polyethylene-polypropylene-copolymer and/or a mixture of polypropylene with polyethylene.

It is preferred for the inner, sealant layer to comprise a high amount of polyolefin, especially polypropylene, in order to benefit from its capacity of being inert towards the stored fluids and for facilitating the manufacturing of a container by means of different welding techniques. It is especially preferred that this layer can form both leaktight, but controllably rupturable, peelable seals at a predetermined temperature and permanent highly consistent seals when welding it together with different conditions such as different welding temperatures or welding pressures.

However, since many conventional polyolefins, in particular polypropylenes, often have an insufficient flexibility and a certain brittleness, it is desirable to combine them with a polymer having an elastic property. In an embodiment according to the present invention, it is therefore preferred to combine the polyolefin of the sealant layer with a supplementary elastomer to improve its flexibility and resilience.

The thermoplastic elastomer that may be compounded with the polyolefin in the inner sealant layer is preferably selected from the group comprising a styrene-ethylene/butylene-styrene-triblock polymer (SEBS), a styrene-ethylene/propylene-styrene-triblock polymer (SEPS), a styrene-butadiene-styrene-triblockpolymer (SBS), and/or a styrene-isoprene-styrene triblock polymer (SIS).

The outer layer preferably comprises a flexible polymeric material with a high melting point that provides the material with an improved stability at the high temperatures locally reached during the welding. Suitable materials can be found among certain polyesters and copolymers thereof (copolyesters) and in particular cycloaliphatic polyesters.

There may be at least one interior layer between the outer layer and the inner sealant layer comprising an thermoplastic elastomer.

Another material that is suitable for the type of containers according to the present invention is Excel™ from McGaw Inc., a multilayered polymeric material of about 200 micrometer thickness which is described in the European patent document EP 0 228 819. Excel™ has a multilayered structure substantially comprising: a) an inner, sealant layer facing the medical fluid consisting of a mixture of a polyethylene/polypropylene copolymer (FINA Dypro Z 9450) and KratonB G1652 from Shell (a styrene/ethylene/butadiene/styrene (SEBS) copolymer); b) a middle, tie layer of pure KratonB G1652; and c) an outer, release layer of Ecdel™ B 9965 (or 9566 or 9967) from Eastman Chemical Co, which is a cycloaliphatic thermoplastic copolyester (a copoly(ester ether), a condensation product of the trans isomer of 1,4-dimethyl-cyclohexanedicarboxylate, of cyclohexanedimethanol and hydroxyterminated polytetramethylene glycol).

Other types of multilayered polymeric films, such as those described above may also be used in the present invention. Such other types of multilayered polymeric films may be made of at least two different polymer layers, wherein the inside layer is a sealant layer that is capable of forming both permanent seals and peelable seals are described in European patent document EP 0 893 982, European patent document EP 0 700 280 and International Publication Number WO 01/42009, as well as methods for their production and methods for welding peelable seals.

The container or bag with peelable seals as described before may be enclosed in an overpouch with a high oxygen barrier. The overpouch film may be a multi-layer structure including PET, a thin glass coating and polypropylene. Suitable overpouches are for example described in European patent document EP 0 893 982. An oxygen absorber may be placed between the container and the overpouch.

An embodiment of the present invention provides a method for forming the inventive container and a method for forming the above described peelable seal. Generally, hot bar heat sealing or impulse heat sealing processes may be used for producing permanent and peelable seals according to the present invention.

Suitable peelable seal welding temperatures for the above mentioned Biofine™ films are in the range of 122 to 130° C. Such seals are suitably leaktight after being subjected to conventional mechanical package tests and are objectively easy to open. They are also suitably leaktight after the container has been subjected to steam sterilization. Suitable welding temperatures for forming permanent seals with Biofine™ film are in the range of 130 to 160° C.

When Excel™ is used as multilayer film material for the manufacture of containers, the temperature for welding peelable seals is 113 to 120° C. and the temperature for welding permanent seals is 130 to 160° C.

In an embodiment of the present invention, the container, as described above, may be used for storing pharmaceutical substances, solutions for dialysis, solutions for infusion and/or agents for nutrition.

BRIEF DESCRIPTION OF THE DRAWINGS

FIG. 4 illustrates a straight peelable seal according to the prior art.

FIG. 5 illustrates a seal with a V-shaped rupture zone according to the prior art.

FIG. 6 illustrates a first preferred embodiment of a seal with a rupture zone according to the present invention.

DETAILED DESCRIPTION

In the following, embodiment examples of the apparatus and method in accordance with the invention are explained in more detail by reference to the drawings.

Figure 1:
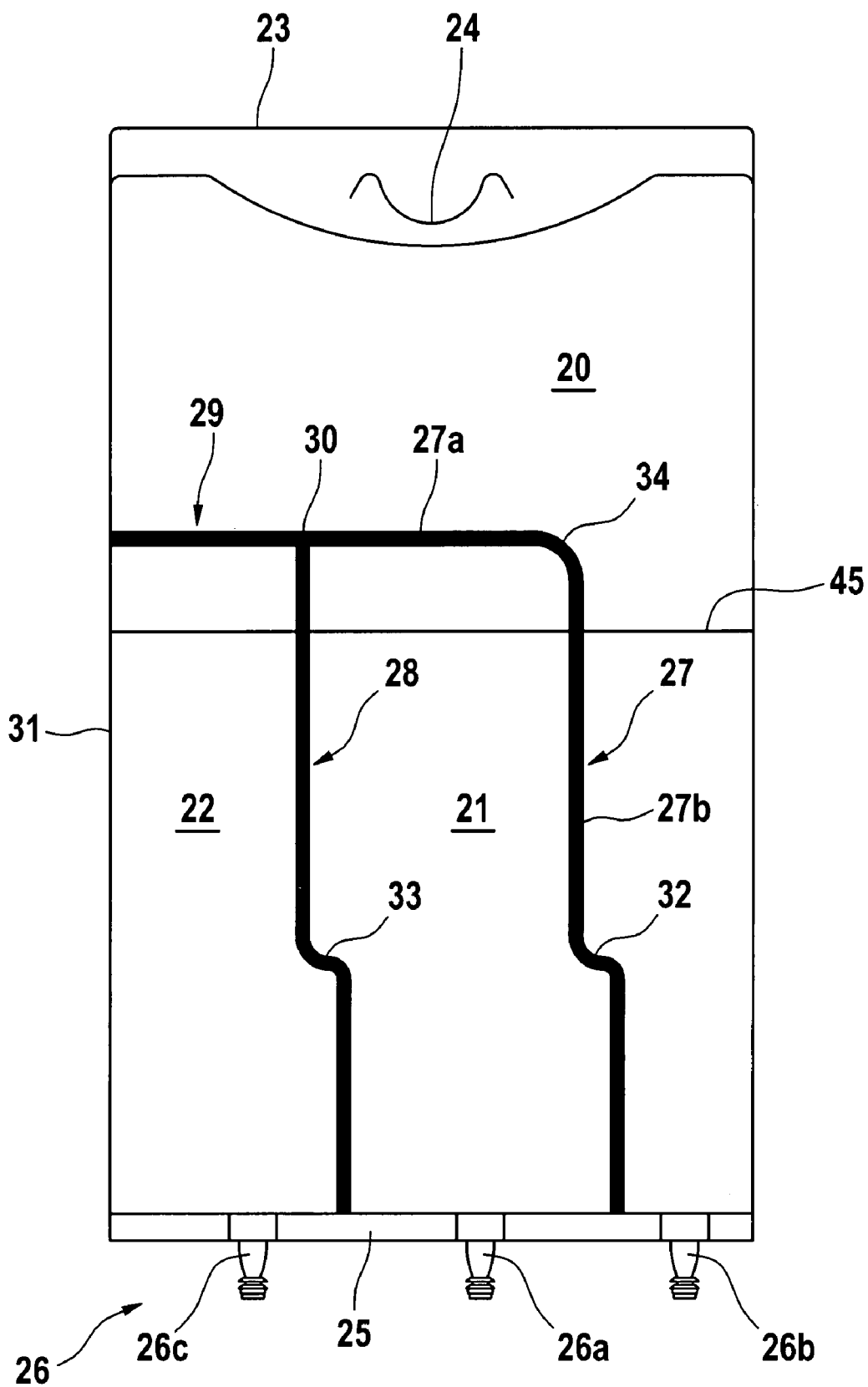
FIG. 1 schematically illustrates a plan view of a first type of container according to the present invention.

Referring now to FIG. 1, a first container according to the present invention is illustrated. The container includes a first chamber 20, a second chamber 21, and a third chamber 22. The three chambers are filled with three different parenterally administrable nutrients in fluid form which, just before their administration to the patient, shall be homogeneously mixed together to form a total parenteral nutrition (TPN) solution. In this embodiment, the first chamber 20 is filled with carbohydrates containing aqueous solution, i.e. glucose, the second chamber 21 is filled with amino acid and/or electrolytes containing aqueous solution and the third chamber 22 with lipid emulsion, i.e. the fat component. It should be noted that although three chambers are present in the embodiment, more chambers can be used. It should also be noted that the contents of the three chambers might vary and that other alternative contents are possible as well. It is according to the invention possible to change the assignment of said ingredients to said chambers. That is, any of the ingredients can be filled in any of the chambers. In another embodiment, chamber 22 contains amino acid solution and chamber 21 contains lipid emulsion. Moreover, electrolytes can also be contained in the carbohydrates containing aqueous solution.

The flexible container is preferably formed from a blown film of 280 or 320 mm width such that only the upper border zone and the lower border zone are sealed together. The upper border zone 23 has a suspension arrangement 24 in the form of an opening so that the container may be hung for bedside administration of the ingredient mixture. The lower border zone 25 has an administration port system 26 for dispensing the medical mixed fluid and introducing supplementary agents according to the patient's requirements.

The administration port system 26 comprises three ports inserted into the lower border zone 25 of the container. All ports can be used for filling the chambers. Moreover, port 26a is also provided as an additive injection port for injecting compatible additives directly into the chamber/chambers using a needle or syringe under aseptic conditions. Port 26b is also provided as an infusion port for administration of the product to the patient. Port 26c is in this preferred embodiment closed with a cap after filling the chamber.

Which type of port that should be connected to the different chambers depends on the arrangement of the ingredients. In the specific embodiment, port 26a is inserted into the lower border zone below the second chamber 21, port 26b below the first chamber 20, and port 26c below the third chamber 22. In another preferred embodiment, the additive port 26a is below third chamber 22. Ports belong to the prior art and are described, e.g. in European patent document EP-A-0 811 560.

The container is made of a multi-layer polypropylene-based film, e.g. as described in European patent document EP-A-0 228 819 or European patent document EP-A-0 739 713 (Biofine™) that can form both peelable seals and permanent seals using hot bar heat sealing or impulse heat sealing process.

The container as a primary bag is enclosed in an overpouch with high oxygen barrier. The overpouch film is a multi-layer structure including PET, a thin glass coating and polypropylene. The thin glass coating provides the oxygen barrier properties. An oxygen absorber is placed between the primary and secondary bags.

The first chamber 20 has a larger volume than the second and third chambers 21, 22, respectively. The first chamber 20 is arranged in the horizontal upper portion as well as in the vertical right side portion of the container, the upper portion extending about ⅓ of the total length between the upper and lower border zones and the right side portion extending about ⅓ of the total width of the container between the right and left border zones. The second chamber 21 is arranged in the vertical middle portion of the container below the upper part of the first chamber, the middle portion extending about ⅓ of the total width of the container. The third chamber 22 is arranged in the vertical left side portion of the container below the upper part of the first chamber, the left side portion extending about ⅓ of the total width of the container.

The three chambers of the container are separated by three highly leaktight welded seams, The first chamber 20 is separated from the second chamber 21 by a first leaktight seam 27 (seal 1), the second chamber 21 is separated from the third chamber 22 by a second leaktight seam 28 (seal 2) and the first chamber 20 is separated from the third chamber 22 by a third leaktight seam 29.

The first seam 274 has a horizontal extending portion 27a as well as a vertical extending portion 27b, whereas the second seam 28 has a vertical extending portion and the third seam 29 has a horizontal extending portion only. The first, second and third seams have a common upper end 30.

In the embodiment, beginning from the left border zone 31 the horizontal third seam 29 extends about ⅓ of the width of the container at about ⅓ of the length of the container between the first and third chambers. Beginning from the end of the third seam 29 the second seam 28 extends in vertical direction to the lower border zone 25 of the container separating the second and third chambers. Also beginning from the end of the third seam 29 the horizontal portion 27a of the first seam 27 extends about ⅓ of the width of the container at about ⅓ of the length of the container, and the vertical portion 27b of the first seam extends from the end of the horizontal portion in vertical direction to the lower border zone 25 separating the first and second chambers.

The first and second seams are formed as peelable seals comprising rupture zones 32, 33. The third seam 29 is preferably also formed as a peelable seal, wherein it has an opening strength that is equal to or higher than the opening strength of the first and second seals, respectively. Seam 29 might, however, also be formed as a permanent seal.

In the specific embodiment, the first peelable seal 27 comprises a first rupture zone 32 zone and the second peelable seal 28 comprises a second rupture zone 33 to avoid ripping the film when opening the seals. The curved opening zones are formed such that the seals slowly open in two steps, i.e. in a first step at the opening zone and in a second step at their other portions.

The transition zone 34 between the horizontal and vertical portions 27a, 27b of the first seam 27 is also formed as a rupture zone 34, but the transition rupture zone has preferably a larger radius of curvature than the other rupture zone 32 of the first peelable seal 27. A larger radius results generally in a higher opening force of the peelable seal, so that generally rupture zone 32 opens before rupture zone 34. The function of the bag is, however, not affected if rupture zone 34 opens before zone 32 as long as seal 27b opens all the way to the bottom of the bag before rupture zone 33 opens.

The rupture zones of both seals can be arranged anywhere from the lower border zone up to the fluid level 45. A preferred placement is at least 50 mm above the border zone 25 (bottom seal) and at least 50 mm below the fluid level 45 of a mixed bag. The optimal placement of the rupture zone is, however, approximately halfway between the lower border zone and the fluid level 45.

The flexible container according to the invention is easy to handle in a controlled manner. In order to mix the solutions for preparation of the parenteral fluid, the container is rolled up from the upper border zone 23 towards the lower border zone 25. By rolling the container up fluid pressure builds up in the chambers. When the pressure is high enough, the first peelable seal 27 opens at the rupture zone 32, i.e. the zone with the smallest radius. By further rolling the container up the fluid pressure further increases and the other portions of the first peelable seal 27 continue to open starting from the rupture zone 32 in both directions. The seal opens down to the lower border zone and up to the fluid level. When the fluid level is reached there is no more pressure on the seal and the seal will not further open. After opening the first seal 27 the second seal 28 is opened at the rupture zone 33. In the same way as for the first seal, the seal opening of the second seal propagates up and down. Therefore, the first and second solutions of the first and second chambers 20, 21, respectively, are mixed in a first step, and the mixture of the first and second solutions and the third solution are mixed in a second step. This is guaranteed by having preferably higher weak seal strength for the third seal with respect to the second and first seal, respectively. If, nevertheless, the third and first seals would have the same seal strength, the curved opening zone of the first seal guarantees the opening of the first seal before the second seal.

Even if the horizontal portions of the seals would have a lower seal strength than the vertical portions, the transition rupture zone 34 of the first seal guarantees the opening of the first seal 27 before the second seal 28.

Figure 2:
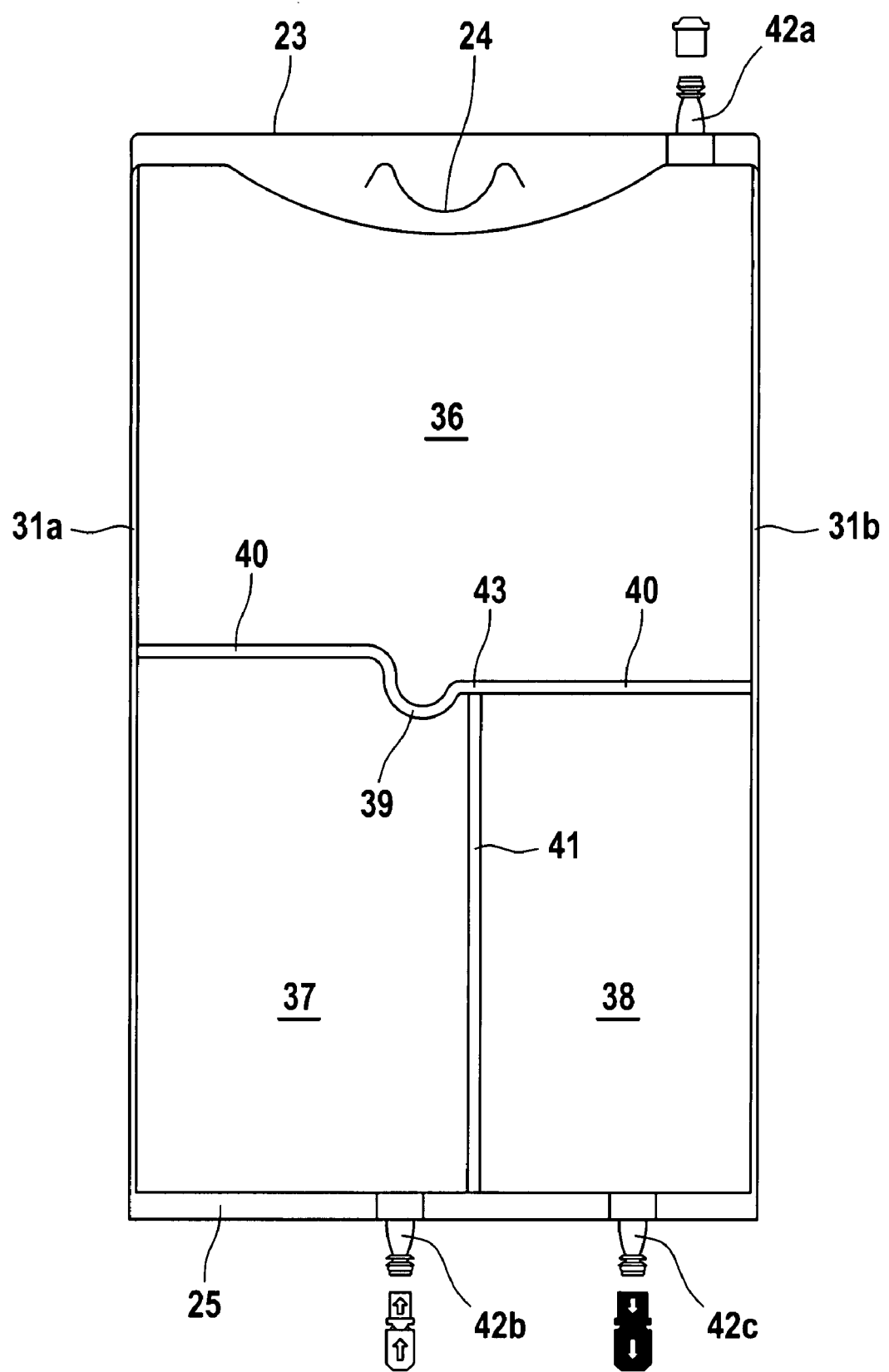
FIG. 2 schematically illustrates a plan view of a second type of container according to the present invention.

FIG. 2 shows another container, according to the present invention, with peelable seals. The container includes a first chamber 36, a second chamber 37 and a third chamber 38, which are separated from each other by leaktight seams 40 and 41. The first chamber is designated to be filled with a first solution, the second chamber is designated to be filled with a second solution and the third chamber is designated to be filled with a third solution. The first chamber 36 is separated from the second and third chambers 37, 38 by a first leaktight seam 40. The second and third chambers are separated from each other by a second leaktight seam 41, wherein both seams 40, 41 have an intersection 43. In the embodiment of FIG. 2, seams 40 and 41 are perpendicular to each other and form a "T".

At least a part of the first seam 40 is provided with a rupture zone 39 according to the present invention, which was described in detail before and which can be opened for fluid communication between the first and at least one of the second or third chambers. The whole leaktight seam 40 might also be formed as a separation zone.

The first chamber 36 has preferably a larger volume than the second and third chambers 37, 38, respectively. The first chamber 36 is preferably arranged in the horizontal upper portion of the container, the upper portion extending about the total width of the container between the right and left border zones 31a and 31b. In the embodiment of FIG. 2, the volume of the first chamber 36 is about the half of the volume of the whole container. A peelable seal 40 with a rupture zone 39 extends horizontally between the border zones 31a and 31b, and in nearly equal distance to the upper border zone 23 and to the lower border zone 25, thereby dividing the container in two halves and separating first chamber 36 from the second and third chambers 37, 38.

The second and third chamber 37, 38 are located in the lower half of the container and separated by a peelable seal 41, which is perpendicular to seal 40 and extends vertically between the peelable seal 40 and the lower border zone 25. Seal 41 might be located in such a way that chambers 37 and 38 have the same volume. In the embodiment shown in FIG. 2, however, second chamber 37 has a larger volume than third chamber 38.

The peelable seal 40 comprises a rupture zone 39 to avoid ripping the film when opening the seal. The rupture zone 39 is in the preferred embodiment of FIG. 2 arranged between chambers 36 and 37. A preferred placement is at least 50 mm away from the border zones 31a and 31b. When first chamber 36 is filled with electrolytes and/or carbohydrate containing aqueous solution, i.e. glucose, the second chamber 37 is filled with amino acid containing aqueous solution and the third chamber 38 with lipid emulsion, the rupture zone is preferably located between chambers 36 and 37, as shown in FIG. 2.

The three chambers are filled with three different parenterally administerable nutrients in fluid form which, just before their administration to the patient, are homogeneously mixed together to form a total parenteral nutrition (TPN) solution. In the embodiment, the first chamber 36 is filled with carbohydrates containing aqueous solution, i.e. glucose, the second chamber 37 is filled with electrolytes and/or amino acid containing aqueous solution and the third chamber 38 with lipid emulsion, i.e. the fat component. It should be noted that although three chambers are present in the embodiment, more chambers can be used. It should also be noted that the contents of the three chambers might vary and that other alternative contents are possible as well. It is according to the invention possible to change the assignment of said ingredients to said chambers. That is, any of the ingredients can be filled in any of the chambers. Moreover, electrolytes may also be contained in the carbohydrates containing aqueous solution.

The flexible container, in the embodiment of FIG. 2, is formed from a blown film such that only the upper border zone and the lower border zone are sealed together. The upper border zone 23 has a suspension arrangement 24 in the form of an opening so that the container may be hung for bedside administration of the ingredient mixture. The chambers 36, 37 and 38 are each provided with one port (42a, 42b, 42c), wherein the ports are located in the upper and lower border zone 23, 25, respectively. The ports 42a, 42b, 42c serve for filling the bag, dispensing the medical mixed fluid and/or introducing supplementary agents according to the patient's requirements.

In the embodiment of FIG. 2, port 42a is provided for filling, port 42b is provided for administration of the bag content to a patient and port 42c is an additive port for injecting additives into the bag. Which type of port that should be connected to the different chambers depends on the arrangement of the ingredients. Ports belong to the prior art and are described, e.g. in European patent document EP-A-0 811 560.

Both leaktight seams are formed as peelable seals. According to the invention, the leaktight seams are arranged and the rupture zone is formed such that, in use of the container for preparation of the medical mixed solution, first seam 40 and the second seam 41, which are formed as peelable seals, open in a sequential order, wherein the opening starts at the rupture zone of the first seam 40. Thereby, the ingredients of the chambers are mixed one after another.

According to the embodiment shown in FIG. 2, the leaktight seams 40, 41 are arranged and the rupture zone 39 is formed such that, in use of the container, for preparation of the medical mixed solution the rupture zone is opened by exerting pressure on the container beginning from the upper portion down to the lower portion of the container. According to a further embodiment, the rupture zone 39 and the seams 40, 41 are peelable seals to be opened by rolling up the container.

By rolling the container from the upper portion down fluid pressure builds up in the first chamber. When the pressure is high enough peelable seals 40, 41 open one after the other so that the fluids are mixed. The arrangement of the peelable seals according to invention allows a controlled mixing and the problem of damage of the container is reduced.

The flexible container, according to the embodiment shown in FIG. 2, is easy to handle in a controlled manner. In order to mix the solutions for preparation of the parenteral fluid, the container is rolled up from the upper border zone 23 towards the lower border zone 25. By rolling the container up, fluid pressure is built up in the chambers. When the pressure is high enough, the peelable seal 40 starts to open at the rupture zone 39, i.e. the zone with the smallest radius. Seal 40 continues to open in direction of the border zone 31a and in direction of the intersection with seal 41. Secondly, the intersection between seal 40 and 41 opens and the opening propagates in direction of the lower border zone 25. A part of seal 40 between seal 41 and seal 31b may remain unopened even though it is peelable.

As a result, the contents of chambers 36 and 37, which are preferably electrolytes and/or carbohydrate containing aqueous solution and amino acid containing aqueous solution, mix in the first step and chamber 38, which preferably contains lipid emulsion, remains closed. In the second step, when the intersection between seal 40 and 41 opens, the third chamber 38 is also opened. Therefore, the first and second solutions of the first and second chambers 36, 37, respectively, are mixed in a first step, and the mixture of the first and second solutions and the third solution in chamber 38 are mixed in a second step.

In principle, all of the polymeric film materials previously described (e.g. Excel™), can be used. The container according to FIG. 2 is made of a multi-layer polypropylene-based film, e.g., as described in European patent document EP-A-0 228 819 or European patent document EP-A-0 739 713 (Biofine™) that can form both peelable seals and permanent seals using hot bar heat sealing or impulse heat sealing process.

The container as a primary bag is enclosed in an overpouch with high oxygen barrier. The overpouch film is a multi-layer structure including PET, a thin glass coating and polypropylene. The thin glass coating provides the oxygen barrier properties. An oxygen absorber is placed between the primary and secondary bags.

Figure 3:
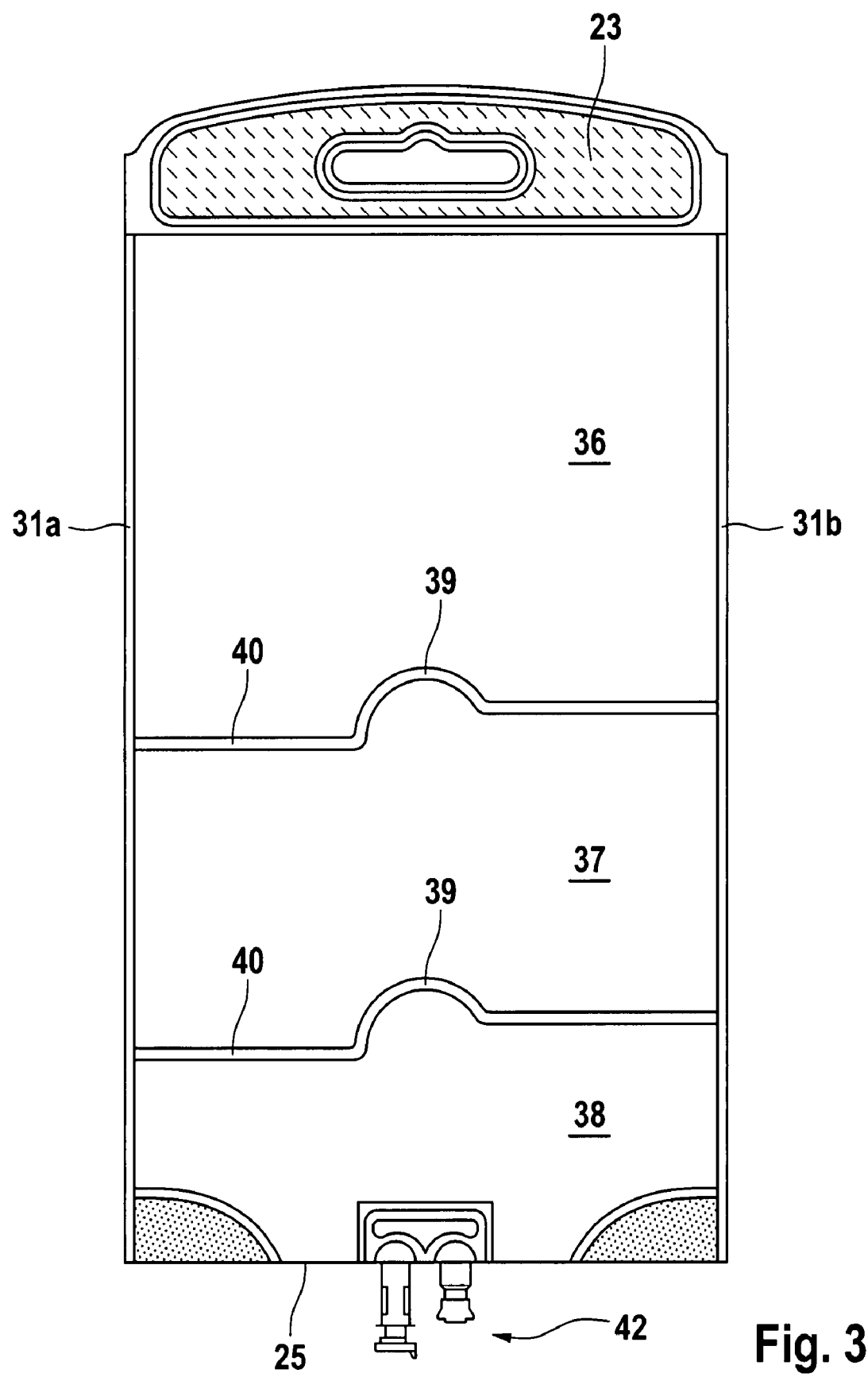
FIG. 3 schematically illustrates a plan view of a third type of container according to the present invention.

FIG. 3 shows another container, according to the present invention, with peelable seals. All reference symbols in FIG. 3 have the same meaning as in FIG. 2. The container is separated into three chambers 36, 37, 38, by two peelable seals 40 with rupture zones 39. The peelable seals both extend horizontally between the border zones 31a and 31b. All three chambers also extend between the border zones 31a and 31b and they are arranged one upon the other. By rolling the container from the from the upper border zone 23 towards the lower border zone 25, fluid pressure is built up in chamber 36. When the pressure is high enough, the upper peelable seal 40 between chamber 36 and 37 opens at the rupture zone 39 and the contents of both chambers can mix in a first step. By further rolling, the lower peelable seal that separates chamber 38 is also opened, and the mixture of the first and second solutions and the third solution in chamber 38 are mixed in a second step.

FIG. 4 shows a straight peelable seal according to the state of the art which has no rupture zone (seal type A). The seal width 14 is 20 mm.

FIG. 5 shows a peelable seal with two straight sections 7, 8 and a V-shaped rupture zone 5 according to the state of the art (seal type B). The seal width 14 is 5 mm, the width 17 of the rupture zone is 150 mm and the height 9 of the rupture zone is 30 mm. Reference symbol 13 stands for the total length of the seal.

FIG. 6 shows, in detail, a shape of a peelable seal according to the present invention (seal type C) with two straight sections 7, 8 and a rupture zone 5. The seal width 14 is 7 mm and the radius 15 is 90 mm. The width 17 of the rupture zone is 145 mm and the height 9 of the rupture zone is 43 mm.

Figure 7:
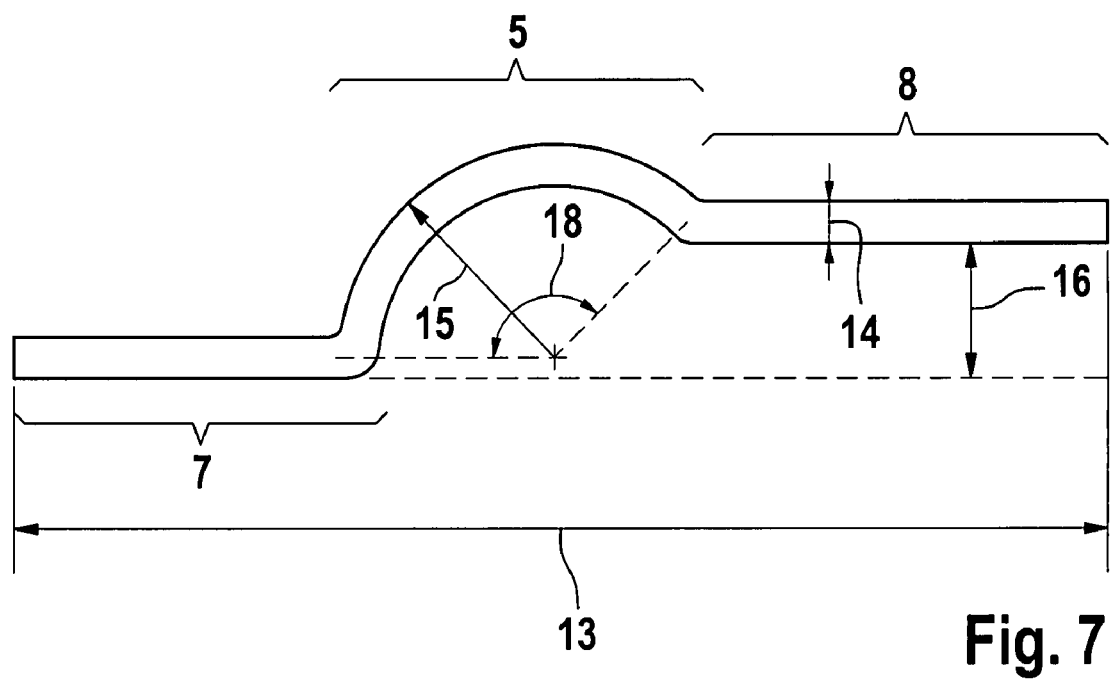
FIG. 7 illustrates a second preferred embodiment of a seal with a rupture zone according to the present invention.

FIG. 7 shows another shape of a peelable seal (seal type D) according to the present invention, wherein the rupture zone 5 is formed as an arc of a circle with a central angle 18 of 145°. The radius 15 is 20 mm. The straight sections 7, 8 are located parallel to each other with an offset 16 of 15 mm. The seal width 14 is 7 mm. Reference symbol 13 stands for the total length of the seal.

Figure 8:
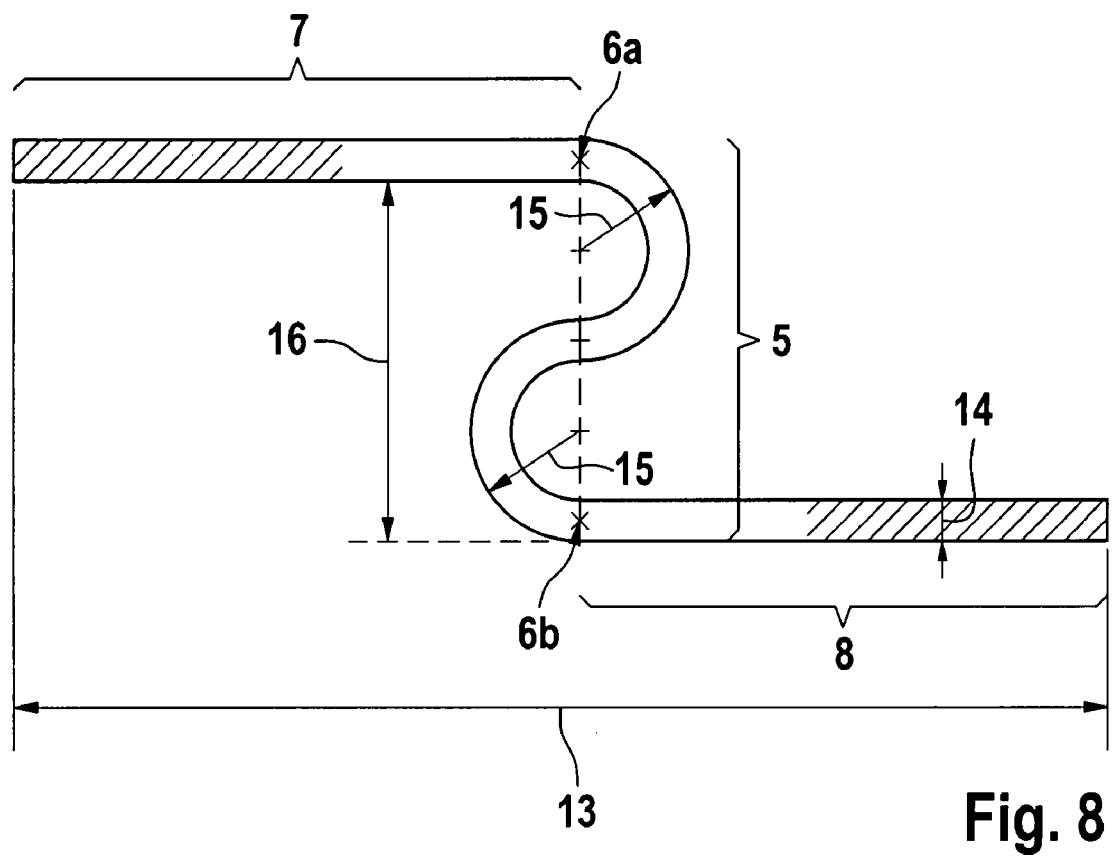
FIG. 8 illustrates a third preferred embodiment of a seal with a rupture zone according to the present invention.

FIG. 8 shows another shape of a peelable according to the present invention (seal type E) with rupture zone 5 that is S-shaped between end points 6a and 6b. The S-shaped rupture zone is formed from two half circles with a radius 15 of 15 mm. The straight sections of the seal 7, 8 are located parallel to each other with an offset 16 of 60 mm. The seal width 14 is 7 mm. Reference symbol 13 stands for the total length of the seal.

Figure 9:
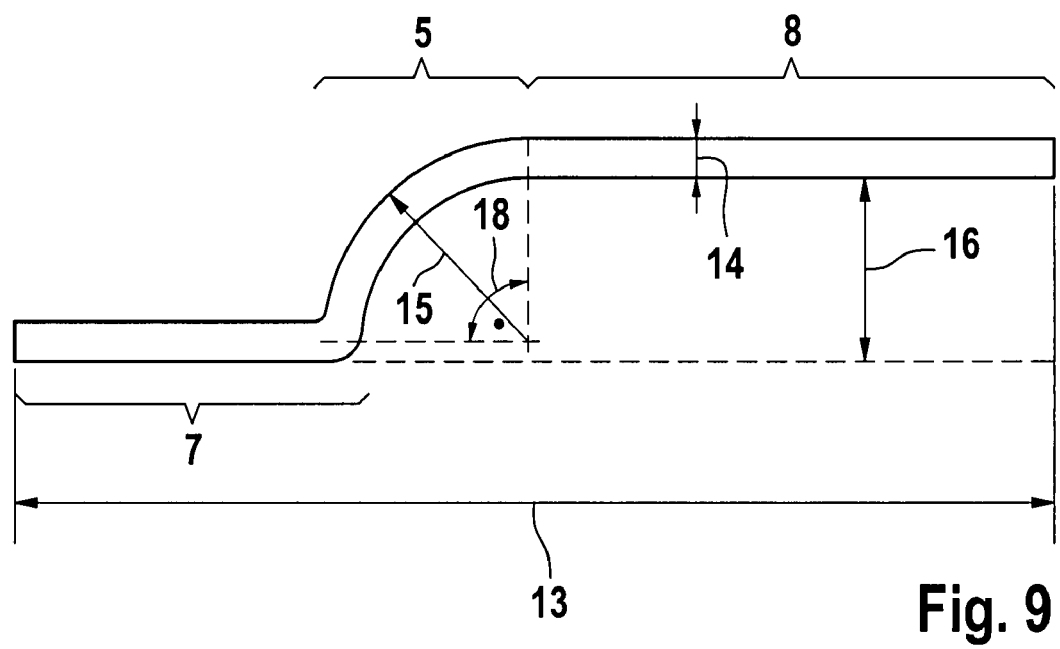
FIG. 9 illustrates a fourth preferred embodiment of a seal with a rupture zone according to the present invention.

FIG. 9 shows another shape of a peelable seal (seal type F) according to the present invention, wherein the rupture zone 5 is formed as an arc of a circle with a central angle 18 of 90°. The radius 15 is 20 mm. The straight sections 7, 8 are located parallel to each other with an offset 16 of 20 mm. The seal width 14 is 7 mm. Reference symbol 13 stands for the total length of the seal.

EXAMPLES

In the following examples the invention is illustrated wherein it is to be understood that these examples do not limit the scope and idea of the invention.

Example 1

A) General Procedure for Forming a Container According to FIG. 3

Containers as shown in FIG. 3 were manufactured from a cast, polyolefin-based film (Excel). The peelable seals were welded at different temperatures from 113-120° C. to achieve different weld strengths, 3 seconds and 4 bar.

Permanent seals were welded at 130° C., 1.5 seconds and 4 bar. Welding was performed with the hot bar technique.

B) Performed Tests

Bags according to FIG. 3 have been manufactured according to the above procedure with different shapes of peelable seals shown in FIGS. 4 to 8. Three different peelable seal strengths were used that were about 10 N, 20 N and 30 N. Every sample group contained 20 bags. 10 bags were filled with water and seven of these were overwrapped and sterilised with a water spray autoclave cycle ($F_0$=12, temperature 121° C.). The following tests have been performed on each sample group.

Figure 10:
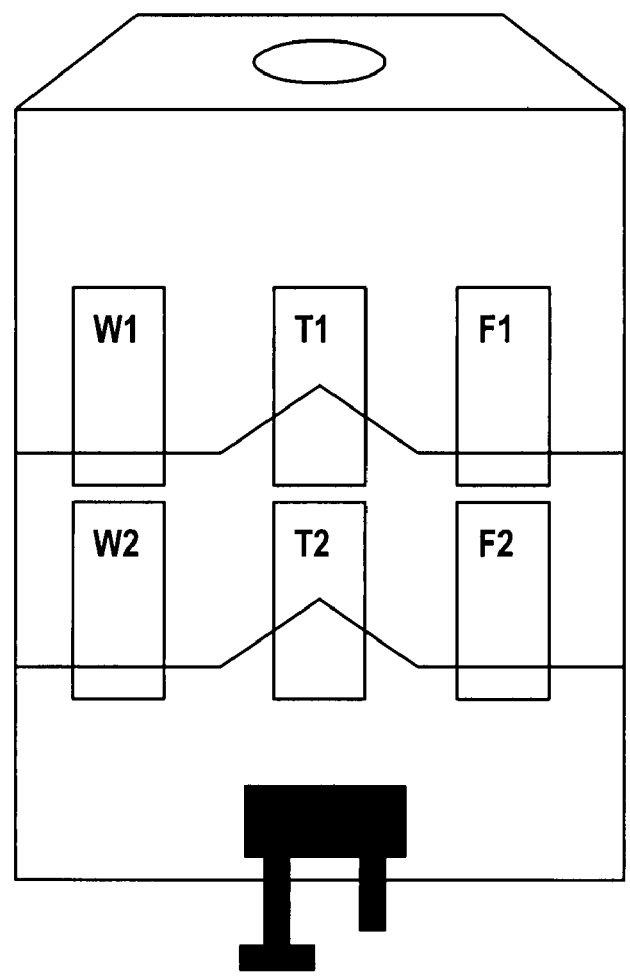
FIG. 10 is an illustration of sampling that shows peelable seal-positions W1, T1, F1, W2, T2, F2 for tensile testing with a container according to FIG. 3 (see Example 1).

Tensile Test:

Tensile test was performed on 30 mm wide strips using an Instron tensile tester. Test strips were taken from position F1, T1, W1 and F2, T2, W2 (see FIG. 10 for positions). Initial grip separation was set to 50 mm. Test speed was set to 500 mm/min. Maximum force was measured.

Non sterilised bags: The seal strength was measured on 5 bags.

Sterilised bags: The seal strength was measured on 2 bags.

Burst Test:

Restrain plates with an opening of 50 millimeter have been used. The pressure has been registered directly inside the bag using a pressure sensor. Incoming pressure has been set to 0.3 bar. The weak seals were opened in peak direction, i.e., seal 1 was opened before seal 2.

Non sterilised bags: Burst test has been performed on 5 bags.

Sterilised bags: Burst test has been performed on 2 bags.

Manual Opening of Bags

The peelable seals are manually opened by the roll method. The degree of difficulty was rated 1 to 5 according to below definition.

1=Very easy
2=Easy
3=Some resistance but no problem to open
4=High resistance but possible to open with big effort
5=Not possible to open Non sterilised bags: Manual opening was performed on 3 bags.

Sterilised bags: Manual opening was performed on 3 bags.

C) Test Results for Different Seal Designs

The tests were performed on bags with different seal shapes A to E as shown in FIGS. 4-8. Seal shapes C to E were inventive examples and shape A was a straight seal reference and shape B was a reference example according to the state of the art of European patent document EP 0 893 982.

Seal Shape A (FIG. 4—Reference Example)

In the table below the total average value for seal strength, measured at 6 positions, is noted.

| Sample ID | Seal strength of non-autoclaved bags (N/30 mm) | Seal strength of autoclaved bags (N/30 mm) |
|---|---|---|
| 10 N | 11 | 43 |
| 20 N | 16 | 42 |
| 30 N | 27 | 43 |

In the table below the average values for the burst test is noted.

| | Burst value of non-autoclaved bags (bar) | | Burst value of autoclaved bags (bar) | |
|---|---|---|---|---|
| Sample ID | Seal 1 | Seal 2 | Seal 1 | Seal 2 |
| 10 N | 0.13 | 0.12 | 0.44 | 0.44 |
| 20 N | 0.20 | 0.18 | >0.55 | >0.55 |
| 30 N | 0.30 | 0.28 | >0.55 | >0.55 |

Seal Shape B (FIG. 5—Reference Example)

In the table below the total average value for seal strength, measured at 6 positions, is noted.

| Sample ID | Seal strength of non-autoclaved bags (N/30 mm) | Seal strength of autoclaved bags (N/30 mm) |
|---|---|---|
| 10 N | 10 | 35 |
| 20 N | 19 | 36 |
| 30 N | 31 | 39 |

In the table below the average values for the burst test is noted.

| | Burst value of non-autoclaved bags (bar) | | Burst value of autoclaved bags (bar) | |
|---|---|---|---|---|
| Sample ID | Seal 1 | Seal 2 | Seal 1 | Seal 2 |
| 10 N | 0.07 | 0.06 | 0.26 | 0.29 |
| 20 N | 0.15 | 0.13 | 0.29 | 0.28 |
| 30 N | 0.24 | 0.23 | 0.29 | 0.27 |

Seal Shape C (FIG. 6)

In the table below the total average value for seal strength, measured at 6 positions, is noted.

| Sample ID | Seal strength of non-autoclaved bags (N/30 mm) | Seal strength of autoclaved bags (N/30 mm) |
|---|---|---|
| 10 N | 13 | 36 |
| 20 N | 19 | 36 |
| 30 N | 29 | 37 |

In the table below the average values for the burst test is noted.

| | Burst value of non-autoclaved bags (bar) | | Burst value of autoclaved bags (bar) | |
|---|---|---|---|---|
| Sample ID | Seal 1 | Seal 2 | Seal 1 | Seal 2 |
| 10 N | 0.08 | 0.09 | 0.30 | 0.30 |
| 20 N | 0.14 | 0.16 | 0.31 | 0.31 |
| 30 N | 0.24 | 0.23 | 0.33 | 0.32 |

Seal Shape D (FIG. 7)

In the table below the total average value for seal strength, measured at 6 positions, is noted.

| Sample ID | Seal strength of non-autoclaved bags (N/30 mm) | Seal strength of autoclaved bags (N/30 mm) |
|---|---|---|
| 10 N | 10 | 37 |
| 20 N | 20 | 37 |
| 30 N | 28 | 41 |

In the table below the average values for the burst test is noted.

| | Burst value of non-autoclaved bags (bar) | | Burst value of autoclaved bags (bar) | |
|---|---|---|---|---|
| Sample ID | Seal 1 | Seal 2 | Seal 1 | Seal 2 |
| 10 N | 0.04 | 0.05 | 0.16 | — |
| 20 N | 0.06 | 0.07 | 0.20 | 0.21 |
| 30 N | 0.10 | 0.11 | 0.22 | 0.25 |

Seal Shape E (FIG. 8)

In the table below the total average value for seal strength, measured at 6 positions, is noted.

| Sample ID | Seal strength of non-autoclaved bags (N/30 mm) | Seal strength of autoclaved bags (N/30 mm) |
|---|---|---|
| 10 N | 14 | 46 |
| 20 N | 21 | 47 |
| 30 N | 35 | 52 |

In the table below the average values for the burst test is noted.

| | Burst value of non-autoclaved bags (bar) | | Burst value of autoclaved bags (bar) | |
|---|---|---|---|---|
| Sample ID | Seal 1 | Seal 2 | Seal 1 | Seal 2 |
| 10 N | 0.05 | 0.05 | — | — |
| 20 N | 0.07 | 0.08 | 0.19 | 0.19 |
| 30 N | 0.14 | 0.12 | 0.22 | 0.20 |

Comparison and Discussion

In the table below a summary for the seal shapes A to E is shown. The degrees of difficulty for manual opening of the bag are listed. The table further shows the maximum seal strength as measured for the different seals and the corresponding burst pressure. The burst pressure values for a seal strength of 20 N/30 mm and 40 N/30 mm were extrapolated in order to allow a better comparison between different seal shapes.

| Seal Shape | Rating for manual opening | Maximum seal strength for easy manual opening (N/30 mm) | Burst pressure at maximum openable seal strength (bar) | Burst pressure at 20 N/30 mm (bar) |
|---|---|---|---|---|
| A (ref.) | 2-4 | 10 | 0.13 | 0.23 |
| B (ref.) | 3 | 30 | 0.23 | 0.15 |
| C | 3 | 30 | 0.25 | 0.15 |
| D | 2-3 | 41 | 0.21 | 0.08 |
| E | 2-3 | 52 | 0.22 | 0.07 |

The results show that a straight peelable seal (shape A) is limited to a low seal strength to remain easily openable. Seals B (reference example according to the state of the art of European patent document EP 0 893 982) and C can be easily opened at higher seal strengths while inventive seal shapes D and E can be easily opened even at high seal strengths. A seal that is easily opened at high seal strengths is preferred from a manufacturing point of view since a high seal strength enhances processability and transportation properties. An infusion bag with a seal strength as low as reference example A requires some kind of support of the seal during transportation, i.e. a fold along the seal line.

A comparison of seals C and D shows that by decreasing the radius of the rupture zone and at the same time adjusting one of the straight sections of the peelable seal parallel to the other thereby creating a gap, seals of a higher strength can be opened.

Example 2

A) General Procedure for Forming a Container According to FIG. 1.

Containers as shown in FIG. 1 were manufactured from a blown tube film (Biofine) based on polyolefins. The peelable seals were welded at different temperatures from 122 to 128° C. to achieve different weld strengths, 3 seconds and 4 bar using the hot bar technique. The rupture zone (peak) was placed at 40 mm, 100 mm and 160 mm from the bottom weld. The total bag length was 400 mm, the bag width was 280 mm and the total length of the peelable seals was 260 mm. The total fluid volume in the bag was 1500 ml.

Permanent seals were impulse welded.

B) Performed Tests

Bags according to FIG. 1 have been manufactured according to the above procedure with different peak positions. Peelable seals were welded at 122, 124, 126 and 128° C. Every sample group contained 10 bags. The bags were not autoclaved. The following tests have been performed on each sample group.

Figure 11:
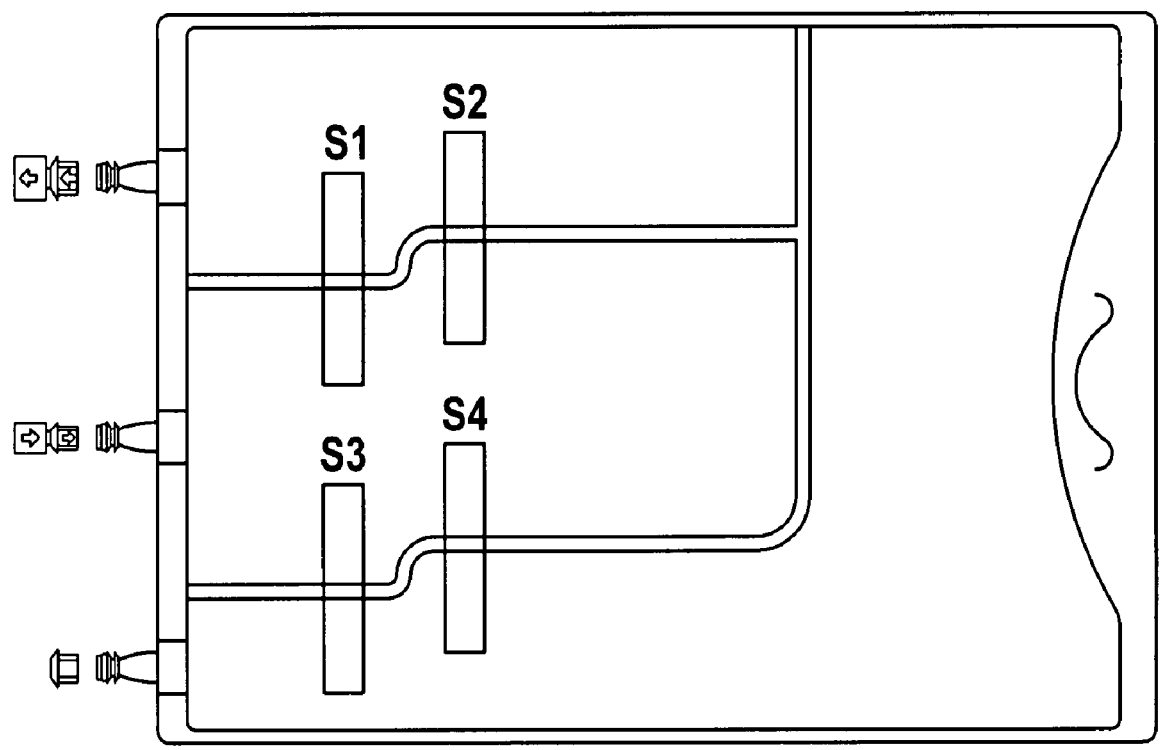
FIG. 11 is an illustration of sampling that shows peelable seal-positions S1, S2, S3 and S4 for tensile testing with a container according to FIG. 1 (see Example 2).

Tensile Test:

Tensile test was performed on 30 mm wide strips using an Instron tensile tester. Test strips were taken from position S1, S2, S3 and S4 (see FIG. 11 for positions). Initial grip separation was set to 50 mm. Test speed was set to 500 mm/min. Maximum force was measured.

The seal strength was measured on 3 bags.

Burst Test:

No restrain plates have been used. The pressure has been registered directly inside the bag using a pressure sensor. Incoming pressure has been set to 0.3 bar. The weak seals were opened in peak direction i.e. seal 1 was opened before seal 2.

Burst test was performed on 3 bags.

Manual Opening of Bags

The peelable seals are manually opened by the roll method. The degree of difficulty was rated 1 to 5 according to below definition.

1=Very easy
2=Easy
3=Some resistance but no problem to open
4=High resistance but possible to open with big effort
5=Not possible to open Manual opening was performed on 4 bags.

C) Test Results for Different Peak Positions

Peak Position 40 mm

In the table below the peelable seal strengths, burst values and ratings for manual opening at different welding temperatures are shown.

| Welding temperature (° C.) | Peelable seal strength (N/30 mm) | Burst value (bar) | | Rating for manual opening | |
|---|---|---|---|---|---|
| | | Seal 1 | Seal 2 | Seal 1 | Seal 2 |
| 122 | 16 | 0.17 | 0.12 | 1.5 | 1.9 |
| 124 | 21 | 0.20 | 0.14 | 2.3 | 3.0 |
| 126 | 26 | 0.25 | 0.17 | 3.0 | 3.3 |
| 128 | 37 | 0.32 | 0.28 | 3.5 | 4.7 |
| 130 | 46 | >0.30 | >0.30 | 5.0 | 5.0 |

Peak Position 100 mm

In the table below the peelable seal strengths, burst values and ratings for manual opening at different welding temperatures are shown.

| Welding temperature | Peelable seal strength | Burst value (bar) | | Rating for manual opening | |
|---|---|---|---|---|---|
| (° C.) | (N/30 mm) | Seal 1 | Seal 2 | Seal 1 | Seal 2 |
| 122 | 16 | 0.12 | 0.09 | 1.0 | 1.0 |
| 124 | 21 | 0.16 | 0.11 | 1.8 | 2.0 |
| 126 | 27 | 0.19 | 0.12 | 1.8 | 2.0 |
| 128 | 37 | 0.28 | 0.16 | 2.5 | 2.7 |
| 130 | 45 | >0.30 | >0.30 | 4.0 | 4.0 |

Peak Position 160 mm

In the table below the peelable seal strengths, burst values and ratings for manual opening at different welding temperatures are shown.

| Welding temperature | Peelable seal strength | Burst value (bar) | | Rating for manual opening | |
|---|---|---|---|---|---|
| (° C.) | (N/30 mm) | Seal 1 | Seal 2 | Seal 1 | Seal 2 |
| 122 | 16 | 0.14 | 0.09 | 1.3 | 2.3 |
| 124 | 21 | 0.17 | 0.10 | 2.0 | 3.5 |
| 126 | 28 | 0.21 | 0.13 | 2.4 | 4.3 |
| 128 | 37 | 0.28 | 0.19 | 3.0 | 5.0 |
| 130 | 45 | >0.30 | >0.30 | 5.0 | 5.0 |

Comparison and Discussion

In the table below a summary for peak positions 40, 100 and 160 mm is shown. The degrees of difficulty for manual opening of the bag are listed at different seal strengths.

| Welding temperature | Peelable seal strength | Rating for manual opening with peak position 40 mm | | Rating for manual opening with peak position 100 mm | | Rating for manual opening with peak position 160 mm | |
|---|---|---|---|---|---|---|---|
| (° C.) | (N/15 mm) | Seal 1 | Seal 2 | Seal 1 | Seal 2 | Seal 1 | Seal 2 |
| 122 | 16 | 1.5 | 1.9 | 1.0 | 1.0 | 1.3 | 2.3 |
| 124 | 21 | 2.3 | 3.0 | 1.8 | 2.0 | 2.0 | 3.5 |
| 126 | 27 | 3.0 | 3.3 | 1.8 | 2.0 | 2.4 | 4.3 |
| 128 | 37 | 3.5 | 4.7 | 2.5 | 2.7 | 3.0 | 5.0 |
| 130 | 45 | 5.0 | 5.0 | 4.0 | 4.0 | 5.0 | 5.0 |

The results show that peelable seals with a high peak position are easier to open than Peelable seals with a low peak position. When the peak position is too high, close to the fluid level of the mixed bag as in peak position 160 mm seal 2 the seal becomes more difficult to open. A comparison of the peak positions evaluated in this example shows that a peak position of 100 mm is the preferred position.

The invention claimed is:

1. A container made of a flexible polymeric film for storing pharmaceutical agents, comprising at least one peelable seal capable of opening along its entire length, the at least one peelable seal including at least two substantially straight sections connected by a curved rupture zone having a first end and a second end, the curved rupture zone curving its entire length between the at least two substantially straight sections, wherein the curved rupture zone forms an arc of a circle having a radius of 5 to 75 mm, the radius extending from the center point of the circle to a point on an outer edge of the at least one peelable seal, wherein the arc of the circle has a central angle, and wherein the at least two substantially straight sections are parallel to each other and offset from each other, and wherein a first straight section of the at least two substantially straight sections extends from the first end of the curved rupture zone in a first direction, and the second straight section of the at least two substantially straight sections extends from the second end of the curved rupture zone in a second opposite direction.

2. The container according to claim 1, wherein the radius is 10 to 30 mm.

3. The container according to claim 1, wherein the radius is 20 to 25 mm.

4. The container according to claim 1, wherein the central angle is at least 60° and is less than 180°.

5. The container according to claim 1, wherein the curved rupture zone is S-shaped.

6. The container according to claim 1, wherein the at least two substantially straight sections have an offset distance of about 5 to 75 mm.

7. The container according to claim 1, wherein a seal width of the at least two substantially straight sections and the rupture zone is from 2 to 10 mm.

8. The container according to claim 1, wherein the container comprises a polymeric film, the container including a first region forming an outside area and a second region forming a sealing inside area, the first region having a higher melting point than the second region, wherein the second region forming the sealing inside area is structured to form both permanent seals and peelable seals when subjected to different welding conditions.

9. The container according to claim 8, wherein the polymeric film comprises at least two layers including an inside layer that is a sealant layer structured to form both permanent seals and peelable seals when subjected to welding at different temperatures.

10. The container according to claim 1, wherein in the container is configured to store at least one of pharmaceutical substances, solutions for dialysis, solutions for infusion and agents for nutrition.

11. The container according to claim 1, wherein the at least one peelable seal is formed between two chambers.

* * * * *